Aug. 18, 1959 K. P. SWANSON Re. 24,687

TOP ROLLS FOR SPINNING MACHINES

Original Filed June 11, 1953

INVENTOR.
KENNETH P. SWANSON

BY
Kenway, Jenney, Witter & Hildreth
ATTORNEYS

United States Patent Office

Re. 24,687
Reissued Aug. 18, 1959

24,687

TOP ROLLS FOR SPINNING MACHINES

Kenneth P. Swanson, Abington, Mass.

Original No. 2,812,554, dated November 12, 1957, Serial No. 361,037, June 11, 1953. Application for reissue December 5, 1957, Serial No. 700,926

3 Claims. (Cl. 19—142)

Figure 1:
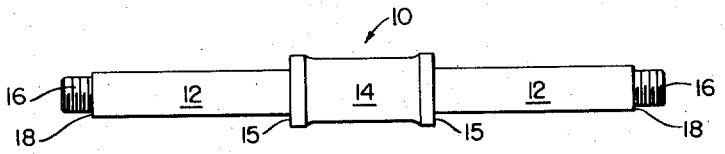

Matter enclosed in heavy brackets [ ] appears in the original patent but forms no part of this reissue specification; matter printed in italics indicates the additions made by reissue.

This application is a continuation-in-part of my application Serial No. 290,704, filed May 29, 1952, now Patent No. 2,704,393. The invention relates particularly to an improved and superior top roll assembly embodying a novel mounting of yarn drafting rolls *adapted* for anti-friction bearing rotation on the two ends of a supporting arbor. Heretofore, such anti-friction bearing assemblies have been complex and so constructed that fine and critical adjustments have been necessary and have thus rendered the assembly expensive and difficult to adjust and maintain. A primary object of my invention resides in the production of a relatively simple construction which requires no adjustment and in which the parts can be conveniently removed and replaced as required.

The improved assembly furthermore includes fixed dust sealing members carried by the arbor and so disposed within the ends of the drawing rolls that dust and lint are prevented from entering the bearings, thereby keeping the bearings clean and preventing the accumulation of lint at the ends of the rolls. The construction of an improved assembly including these novel features comprises a further object of the invention.

These and other features of the invention will be best understood and appreciated from the following description of preferred embodiments thereof selected for purposes of illustration and shown in the accompanying drawing in which—

Figure 2:
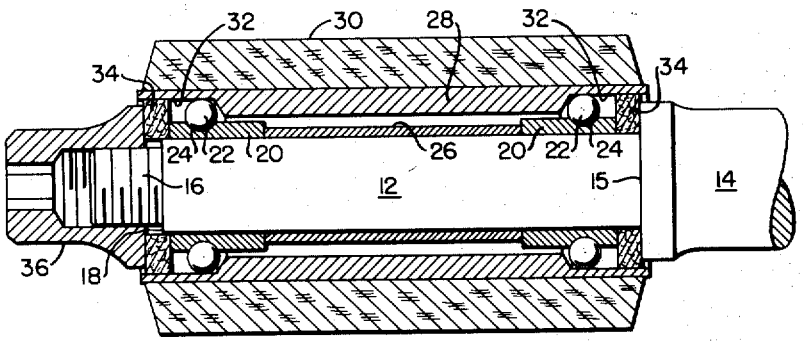
Figure 3:
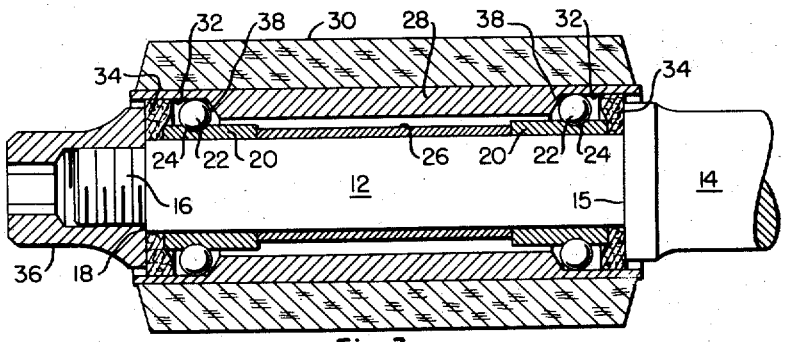
Figure 4:
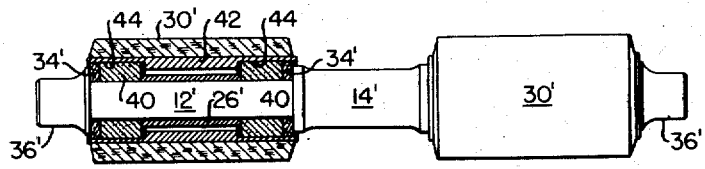

Fig. 1 is an elevation of [the] *a* supporting arbor employed in my improved top roll assembly, Fig. 2 is an enlarged fragmentary view illustrating in longitudinal section a preferred embodiment of the invention, Fig. 3 is a like view showing the parts tightened to operative position, and Fig. 4 illustrates in side elevation and in section a modified construction.

[The] *A* supporting arbor 10 for my improved top roll assembly is illustrated in Fig. 1 and comprises two coaxial end portions 12 at opposite sides of a middle section 14 of greater diameter and providing an outwardly facing annular shoulder 15 at the junction of each end portion with the middle section. A threaded stud 16 of reduced diameter is integral with and projects outwardly beyond the free end of each end portion 12 and provides an outwardly facing annular shoulder 18 at the junction of each stud with its end portion.

A drafting assembly is mounted on each end portion 12, as illustrated in Fig. 4, and each comprises a tubular yarn drawing roll rotatably supported on the anti-friction bearings on the end portion.

A preferred form of the invention is illustrated in Figs. 2 and 3 of the drawing. Two ball bearing races each including a sleeve 20 and ball bearings 22 disposed annularly about each sleeve within a raceway 24 are mounted in spaced relation on each end portion 12. A tubular spacer *sleeve* 26 is disposed on each portion 12 between the two sleeves. A tubular drawing roll is rotatably supported on the ball races over each portion 12 and each *of these rolls* comprises a cylindrical supporting sleeve 28 within *and supporting* a tubular cot 30. The sleeve 28 is reamed out at 32 at its ends to accommodate the ball bearings 22. Also disposed on the ends of each portion 12 are two annular dust sealing members 34 of felt or other resiliently compressible material.

In Fig. 2 the parts are shown in assembled relation with a binding nut 36 in place on the stud 16. The sealing rings 34 normally expand to the thickness illustrated in Fig. 2 and the overall length of the rings together with the sleeves 20 and spacer *sleeve* 26 exceeds the length of the end portion 12. When the nut 36 is tightened into contact with the shoulder 18 (Fig. 3) the two rings 34 are compressed against the shoulders 15 and 18 and thus held from rotation together with the sleeve 20 and spacer *sleeve* 26. The rings are of a size to fit loosely within the reamed out ends 32 of the sleeve 28, thereby keeping the bearings clean and preventing the accumulation of lint which would otherwise gather on rotary parts at the ends of the roll and interfere with its free rotation. The balls 22 and sleeve 28 have a slight clearance at 38 that permits free rotation of the roll.

The assembly shown in Fig. 4 is substantially the same as shown in Figs. 2 and 3 and above described, except that anti-friction bearings 40 of the "Oilite" sleeve type are employed in lieu of ball bearings. In this case the cylindrical sleeve 42 is reamed out at 44 to receive and rest on the bearings 40 and to loosely receive the dust sealing rings 34'. The assembly and its functioning are otherwise like that shown in Figs. 2 and 3 and like parts are indicated by like reference characters primed.

My improved assembly employs few and relatively simple and inexpensive parts which parts are easily and conveniently assembled and disassembled. The drawing rolls are mounted to rotate freely on the arbor bearings and are supported against axial movement without the requirement of fine tolerances necessary in the anti-friction assemblies heretofore known. It will be apparent that the entire unit on each end of the arbor, including the two bearing sleeves and spacer and the two dust sealing rings at the ends of the drawing roll, is fixed against rotation. Thus the fixed sealing rings 34 and 34' permit free rotation of the rolls without the accumulation and clogging of lint at the bearings and they protect the entire bearing unit against exposure, thereby continuously maintaining the rolls freely rotatable on the fixed bearing units and without any pressure on the bearing rolls other than the weight of the rotary rolls or bosses.

Having thus disclosed my invention what I claim as new and desire to secure by Letters Patent is:

1. A top roll assembly for textile drafting machines, comprising an arbor embodying two coaxial end portions at opposite sides of a middle section of greater diameter and providing an outwardly facing annular shoulder at the junction of each end portion with the middle section, a threaded stud integral with and projecting outwardly beyond the free end of each end portion, and a drafting assembly mounted on each of said end portions and each comprising two spaced anti-friction bearings including two bearing sleeves on and respectively at the ends of its end portion, a tubular spacer on the end portion between and in end to end abutting relation with the sleeves, a tubular drawing roll rotatably supported coaxially on the bearings in spaced relation outwardly from the spacer, two annular dust sealing members disposed *on the arbor* respectively [on] *at* the ends of the end portion and loosely fitting within and with their peripheries in *annular* contact with the ends of the drawing roll, and a nut threaded to the stud of each end portion and binding non-rotatably and into a unit on the end portion and between said outer facing annular shoulder and the nut the two dust sealing members, the two bearing sleeves and the spacer therebetween all in pressure abutting relation.

2. The top roll assembly defined in claim 1 in which said sealing members are resiliently compressible and each end portion is provided with an outwardly facing annular shoulder at the junction of its stud therewith, and in which each nut is in tight contact with the adjacent annular shoulder and the portions of the sealing members disposed in contact with the bearing sleeves are compressed to a thickness substantially less than the thickness at the peripheral portions in contact with the drawing roll.

*3. Top roll construction for textile drafting machines, comprising a cylindrical arbor, means forming an annular external flange about an intermediate portion of the arbor, said arbor having a threaded end, a tubular drawing roll having end portions reduced to form internal shoulders, sleeves on said arbor, one set of bearing balls mounted in spaced relation upon each of two of said sleeves, said sleeves being carried in abutting relation upon said arbor and dimensioned to space the sets of balls apart by a distance greater than the distance between the internal shoulders of the tubular drawing roll, a first lint sealing ring mounted on the arbor adjacent*

*said annular flange and one end of one of said sleeves, a second lint sealing ring mounted on said arbor adjacent said threaded portion and the end of another sleeve, and means threaded on the threaded end of the arbor for exerting axial pressure on said sleeves and flange to bind the sleeves against rotation about said arbor, said drawing roll being supported for rotation upon said sets of balls with axial clearance between said sets of balls and the internal shoulders of the drawing roll.*

References Cited in the file of this patent or the original patent

UNITED STATES PATENTS

| | | |
|---|---|---|
| 594,605 | Collins | Nov. 30, 1897 |
| 762,081 | McNulty | June 7, 1904 |
| 981,307 | Ragsdale | Jan. 10, 1911 |
| 2,237,004 | King | Apr. 1, 1941 |
| 2,584,640 | Taylor | Feb. 5, 1952 |
| 2,635,300 | Butler | Apr. 21, 1953 |
| 2,644,202 | Cotchett | July 7, 1953 |
| 2,716,780 | Swanson | Sept. 6, 1955 |
| 2,724,623 | Robinson et al. | Nov. 22, 1955 |
| 2,755,515 | Cotchett et al. | July 24, 1956 |

FOREIGN PATENTS

| | | |
|---|---|---|
| 22,170 | Great Britain | of 1891 |
| 454,536 | Italy | Jan. 24, 1950 |